United States Patent
Chen

[11] Patent Number: 6,008,352
[45] Date of Patent: Dec. 28, 1999

[54] 1-(ISOQUINOLIN-1-YL)-4-(1-PHENYLMETHYL) PIPERAZINES; DOPAMINE RECEPTOR SUBTYPE SPECIFIC LIGANDS

[75] Inventor: Xi Chen, Clinton, Conn.

[73] Assignee: Neurogen Corporation, Branford, Conn.

[21] Appl. No.: 09/034,189

[22] Filed: Mar. 3, 1998

Related U.S. Application Data

[60] Provisional application No. 60/039,289, Mar. 4, 1997.
[51] Int. Cl.$^6$ ........................ C07D 401/04; C07D 405/14
[52] U.S. Cl. ......................................... 544/363; 514/254
[58] Field of Search ............................. 544/363

[56] References Cited

U.S. PATENT DOCUMENTS 4,590,273   5/1986   Konz et al. .............................. 544/363

FOREIGN PATENT DOCUMENTS 512755   11/1992   European Pat. Off. .
9839301   9/1998   WIPO .

*Primary Examiner*—Emily Bernhardt
*Attorney, Agent, or Firm*—McDonnell, Boehnen Hulbert & Berghoff

[57] ABSTRACT

Disclosed are compounds useful in treating psychotic disorders such as schizophrenia and other central nervous system diseases, where the compounds have general Formula I:

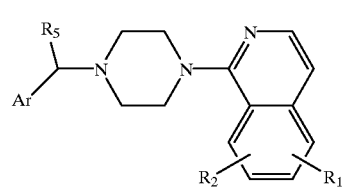

wherein:
Ar represents an aryl or heteroaryl group;
$R_1$ and $R_2$ independently represent hydrogen, halogen, $C_1$–$C_6$ alkyl, $C_1$–$C_4$ alkoxy, $C_1$–$C_4$ alkylthio, hydroxy, amino, mono- or di($C_1$–$C_6$)alkyl amino, cyano or trifluoromethyl; and
$R_5$ represents hydrogen or $C_1$–$C_6$ alkyl.

14 Claims, No Drawings

1-(ISOQUINOLIN-1-YL)-4-(1-PHENYLMETHYL) PIPERAZINES; DOPAMINE RECEPTOR SUBTYPE SPECIFIC LIGANDS

This application claims the benefit of U.S. Provisional Application Ser. No. 60/039,289 filed Mar. 4, 1997.

BACKGROUND OF THE INVENTION

1. Field of the Invention

This invention relates to 1-(isoquinolin-1-yl)-4-(1-phenylmethyl)piperazines and pharmaceutical compositions and preparations containing such compounds. It also relates to the use of such compounds in the treatment or prevention of psychotic disorders such as schizophrenia and other central nervous system diseases.

2. Description of the Related Art

The therapeutic effect of conventional antipsychotics, known as neuroleptics, is generally believed to be exerted through blockade of dopamine receptors. However, neuroleptics are frequently responsible for undesirable extrapyramidal side effects (EPS) and tardive dyskinesias, which are attributed to blockade of $D_2$ receptors in the striatal region of the brain. The dopamine $D_4$ receptor subtype has recently been identified (Sokoloff, P. et al., *Nature,* 1990, 347, 146). Its unique localization in limbic brain areas and its differential recognition of various antipsychotics suggest that the $D_4$ receptor may play a major role in the etiology of schizophrenia Selective $D_4$ antagonists are considered effective antipsychotics free from the neurological side effects displayed by conventional neuroleptics.

European Patent Application EP 512755 A2 discloses piperazine derivatives said to be $5\text{-}HT_{1a}$ antagonists.

SUMMARY OF THE INVENTION

This invention provides novel compounds of Formula I which interact with dopamine receptor subtypes. A broad aspect of the invention is directed to compounds of Formula I:

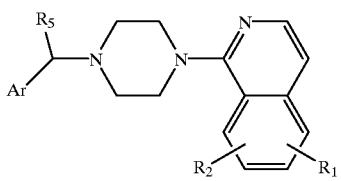

I wherein:
Ar represents an optionally substituted heteroaryl group or an optionally substituted aryl group;
$R_1$ and $R_2$ independently represent hydrogen, halogen, $C_1$–$C_6$ alkyl, $C_1$–$C_4$ alkoxy, $C_1$–$C_4$ alkylthio, hydroxy, amino, mono- or di($C_1$–$C_6$)alkyl amino, cyano or trifluoromethyl; and
$R_5$ represents hydrogen or $C_1$–$C_6$ alkyl.

In this aspect, when Ar is phenyl, it is not an unsubstituted phenyl group. In other words, where Ar is phenyl, the phenyl is substituted with at least one non-hydrogen group.

In yet another aspect, the invention provides pharmaceutical compositions comprising compounds of Formula I.

Since dopamine $D_4$ receptors are concentrated in the limbic system (Taubes, *Science* 265: 1034, 1994) which controls cognition and emotion, compounds which interact with these receptors are useful in the treatment of cognitive disorders. Such disorders include cognitive deficits which are a significant component of the negative symptoms (social withdrawal and unresponsiveness) of schizophrenia. In addition, disorders involving memory impairment or attention deficit disorders can be treated with the compounds of this invention. These compounds interact specifically with the dopamine $D_4$ receptor subtype.

The compounds of the invention demonstrate high affinity and selectivity in binding to the $D_4$ receptor subtype. The use of the compounds of this invention in methods of treating neuropsychological disorders is predicated on the ability of the compounds to bind selectively to a dopamine receptor subtype, the $D_4$ receptor. The compounds of the invention can therefore be used in the treatment of schizophrenia, psychotic depression and mania. Other dopamine-mediated diseases such as Parkinsonism and tardive dyskinesias can also be treated directly or indirectly by modulation of $D_4$ receptors.

Thus, in another aspect, the invention provides methods for treating and/or preventing neuropsychological disorders including, for example, schizophrenia, mania, dementia, depression, anxiety, compulsive behavior, substance abuse, memory impairment, cognitive deficits, Parkinson-like motor disorders and motion disorders related to the use of neuroleptic agents. It also provides methods of treating affective disorders such as Alzheimer's disease and certain movement disorders such as Parkinsonism and dystonia.

The invention further provides methods for treating the extrapyramidal side effects associated with the use of conventional neuroleptic agents. The compounds of the present invention are also useful for the treatment of other disorders which respond to dopaminergic blockade such as substance abuse and obsessive compulsive disorder.

DETAILED DESCRIPTION OF THE INVENTION

In addition to compounds of Formula I, the invention provides compounds of Formula IA:

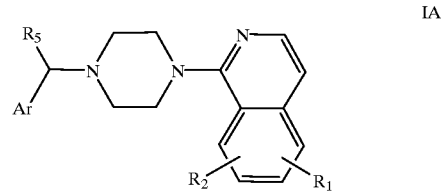

IA wherein:
Ar represents aryl or heteroaryl, each of which is optionally substituted with $R_3$ and/or $R_4$, provided that Ar is not unsubstituted phenyl;
$R_1$ and $R_2$ independently represent hydrogen, halogen, $C_1$–$C_6$ alkyl, $C_1$–$C_4$ alkoxy, $C_1$–$C_4$ alkylthio, hydroxy, amino, mono- or di($C_1$–$C_6$)alkyl amino, cyano or trifluoromethyl; and
$R_5$ represents hydrogen or $C_1$–$C_6$ alkyl.

Preferred compounds of Formula IA are those where $R_3$ and $R_4$ independently represent hydrogen, halogen, hydroxy, $C_1$–$C_6$ alkyl, trifluoromethyl, trifluoromethoxy or $SO_2NH_2$, with the proviso provided that not both $R_3$ and $R_4$ are hydrogen simultaneously; or $R_3$ and $R_4$ together represent an alkylene, alkenylene, alkyleneoxy, or alkylenedioxy chain that together with the atoms to which they are attached form a ring having 5–7 ring atoms.

In compound IA, $R_3$ is preferably in a position para to the point of attachment of the aryl or heteroaryl group to the methylene group.

Thus, in the compounds of the invention, Ar is not unsubstituted phenyl since a substituent on the phenyl group is required for activity at the $D_4$ receptor. I.e., phenyl must contain at least one non-hydrogen substituent. Suitable non-hydrogen substituents are the non-hydrogen $R_3$ and $R_4$ substituents defined above.

Preferred Ar groups of Formulas I and IA are

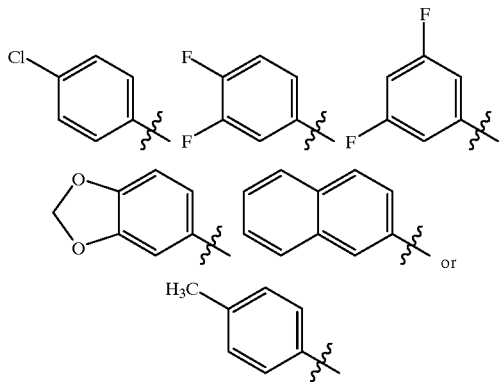

In addition to compounds of Formula I above, the invention provides compounds of Formula II:

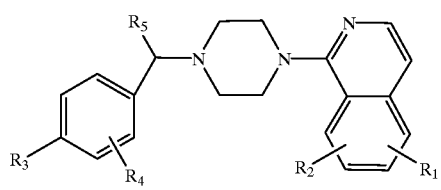

wherein:

$R_1$ and $R_2$ independently represent hydrogen, halogen, $C_1$–$C_6$ alkyl, $C_1$–$C_4$ alkoxy, $C_1$–$C_4$ alkylthio, hydroxy, amino, mono- or di($C_1$–$C_6$)alkyl amino, cyano or trifluoromethyl;

$R_3$ and $R_4$ independently represent hydrogen, halogen, hydroxy, $C_1$–$C_6$ alkyl, trifluoromethyl, trifluoromethoxy or $SO_2NH_2$, with the proviso provided that not both $R_3$ and $R_4$ are hydrogen simultaneously; and $R_5$ represents hydrogen or $C_1$–$C_6$ alkyl.

In preferred compounds of Formula II, at least one of $R_3$ and $R_4$ is $C_1$–$C_6$ alkyl or halogen. In more preferred compounds of Formula II, $R_5$ is hydrogen, and $R_3$ and $R_4$ are independently hydrogen or $C_1$–$C_6$ alkyl. In still other more preferred compounds of Formula II, $R_5$ is hydrogen, and $R_3$ and $R_4$ are hydrogen and halogen, respectively, or are both halogen.

In still other preferred compounds of Formula II, the phenyl group (Ar) is substituted with methyl or mono- or disubstituted with halogen, and $R_5$ is hydrogen.

The most preferred compounds of Formula II are those where $R_1$ and $R_2$ are both hydrogen.

Particularly preferred compounds of Formula II are those where $R_1$ and $R_2$ are hydrogen and the phenyl group (Ar) is monosubstituted in the 4 position with methyl or chloro (4-methylphenyl or 4-chlorophenyl) or the phenyl group is disubstituted with fluoro in both the 3 and 4-positions (3,4-difluorophenyl).

The invention also provides compounds of Formula III:

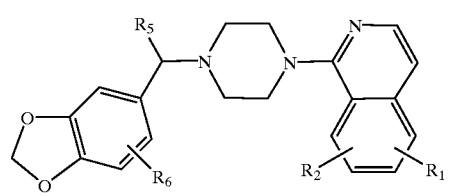

wherein:

$R_1$ and $R_2$ independently represent hydrogen, halogen, $C_1$–$C_6$ alkyl, $C_1$–$C_4$ alkoxy, $C_1$–$C_4$ alkylthio, hydroxy, amino, mono- or di($C_1$–$C_6$)alkyl amino, cyano or trifluoromethyl;

$R_6$ represents hydrogen, halogen, hydroxy, $C_1$–$C_6$ alkyl, trifluoromethyl, trifluoromethoxy or $SO_2NH_2$; and $R_5$ represents hydrogen or $C_1$–$C_6$ alkyl.

In preferred compounds of Formula III, $R_6$ is hydrogen, $C_1$–$C_6$ alkyl, or halogen. In more preferred compounds of Formula IV, $R_5$ is hydrogen and $R_6$ is hydrogen, $C_1$–$C_6$ alkyl, or halogen. In still other preferred compounds of Formula III, $R_1$ and $R_2$ are halogen, $C_1$–$C_6$ alkyl, or hydroxy, $R_5$ is hydrogen and $R_6$ is hydrogen, $C_1$–$C_6$ alkyl, or halogen.

The most preferred compounds of Formula III are those where $R_1$ and $R_2$ are both hydrogen, and $R_5$ and $R_6$ are hydrogen.

The invention also provides compounds of Formula IV:

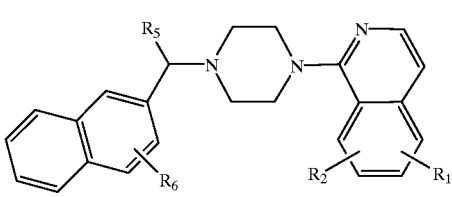

wherein:

$R_1$ and $R_2$ independently represent hydrogen, halogen, $C_1$–$C_6$ alkyl, $C_1$–$C_4$ alkoxy, $C_1$–$C_4$ alkylthio, hydroxy, amino, mono- or di($C_1$–$C_6$)alkyl amino, cyano or trifluoromethyl;

$R_6$ represents hydrogen, halogen, hydroxy, $C_1$–$C_6$ alkyl, trifluoromethyl, trifluoromethoxy or $SO_2NH_2$; and $R_5$ represents hydrogen or $C_1$–$C_6$ alkyl.

In preferred compounds of Formula IV, $R_6$ is hydrogen, $C_1$–$C_6$ alkyl, or halogen. In more preferred compounds of Formula IV, $R_5$ is hydrogen and $R_6$ is hydrogen, $C_1$–$C_6$ alkyl, or halogen. In still other preferred compounds of Formula IV, $R_1$ and $R_2$ are halogen, $C_1$–$C_6$ alkyl, or hydroxy, $R_5$ is hydrogen and $R_6$ is hydrogen, $C_1$–$C_6$ alkyl, or halogen.

The most preferred compounds of Formula IV are those where $R_1$ and $R_2$ are both hydrogen, and $R_5$ and $R_6$ are hydrogen.

In certain situation, compounds of Formula I may contain one or more asymmetric carbon atoms, so that the compounds can exist in different stereoisomeric forms. These compounds can be, for example, racemates or optically active forms. For example, where $R_5$ in Formula I is a methyl group, the resulting compound can be present as (R) and (S) stereoisomers. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral HPLC column.

Representative compounds of the present invention, which are encompassed by Formula I, include, but are not limited to the compounds in Table I and their pharmaceutically acceptable salts. If the compound of the invention is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds.

Non-toxic pharmaceutically acceptable salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as, for example, acetic, $HOOC-(CH_2)_n-COOH$ where n is 0–4, such as, for example, oxalic (n=0), and the like. Those skilled in the art will recognize a wide variety of non-toxic pharmaceutically acceptable addition salts.

The present invention also encompasses the acylated prodrugs of the compounds of Formula I. Those skilled in the art will recognize various synthetic methodologies which may be employed to prepare non-toxic pharmaceutically acceptable addition salts and acylated prodrugs of the compounds encompassed by Formula I.

By the terms $(C_1-C_6)$alkyl and lower alkyl is meant straight and branched chain alkyl groups having from 1–6 carbon atoms as well as cyclic alkyl groups such as, for example, cyclopropyl, cyclobutyl, or cyclohexyl. Specific examples of such alkyl groups are methyl, ethyl, propyl, isopropyl, n-butyl, isobutyl, tert-butyl, sec-butyl, neopentyl and n-pentyl. Preferred $C_1-C_6$ alkyl groups are methyl, ethyl, propyl, butyl or cyclopropylmethyl.

By the terms $(C_1-C_6)$alkoxy and lower alkoxy is meant straight and branched chain alkoxy groups having from 1–6 carbon atoms.

By hydroxy $C_1-C_6$ alkyl is meant a $C_1-C_6$ alkyl group carrying a terminal hydroxy moiety.

By the term piperonyl as used herein is meant a group of the Formula:

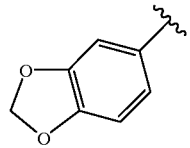

By halogen, halo, or halide is meant fluorine, chlorine, bromine and iodine substituents.

By aryl or "Ar" is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl, anthryl, or phenanthryl), which is optionally mono-, di-, or trisubstituted with, e.g., halogen, lower alkyl, lower alkoxy, lower alkylthio, trifluoromethyl, lower acyloxy, aryl, heteroaryl, and hydroxy.

By aryl or "Ar" is also meant heteroaryl groups where heteroaryl is defined as 5, 6, or 7 membered aromatic ring systems having at least one hetero atom selected from the group consisting of nitrogen, oxygen and sulfur. Examples of heteroaryl groups are pyridyl, pyrimidinyl, pyrrolyl, pyrazolyl, pyrazinyl, pyridazinyl, oxazolyl, furanyl, quinolinyl, isoquinolinyl, thiazolyl, and thienyl, which can optionally be substituted with, e.g., halogen, lower alkyl, lower alkoxy, lower alkylthio, trifluoromethyl, lower acyloxy, aryl, heteroaryl, and hydroxy.

As noted above, $R_3$ and $R_4$ may be connected together to form another ring with the atoms to which they are attached on the parent aryl or heteroaryl group. Thus, $R_3$ and $R_4$ may represent an alkylene, alkenylene, alkyleneoxy, or alkylenedioxy chain that together with the atoms to which they are attached form a ring having 5–7 atoms. For example, Ar may be an optionally substituted naphthyl group or a bicyclic oxygen-containing group of the formula

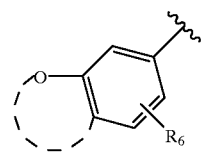

wherein the heterocyclic oxygen containing ring has a total of from 5 to 7 ring members, the heterocyclic ring being saturated or unsaturated, and optionally substituted. $R_6$ is as defined above for Formula III.

Preferred examples of bicyclic oxygen-containing groups are:

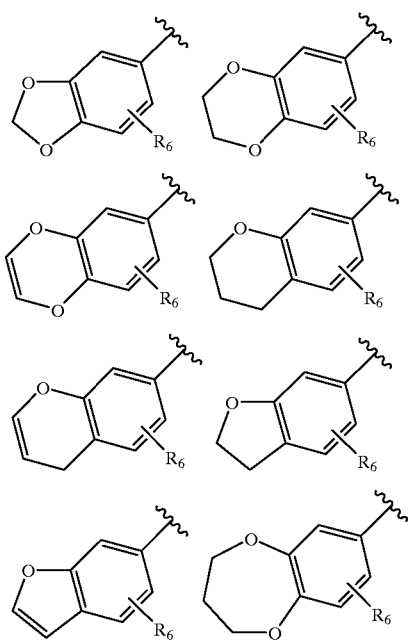

Representative examples of isoquinolinylpiperazines according to the invention are shown in Table 1 below.

TABLE 1

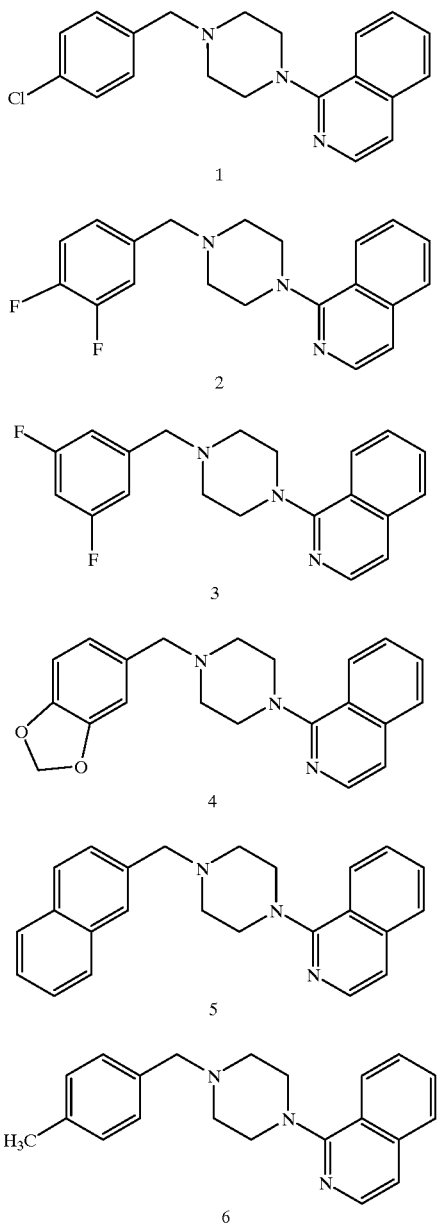

The number in Table 1 below each structure is its compound number.

As noted above, the invention also pertains to the use of compounds of general Formula I in the treatment of various neuropsychological disorders.

The compounds of general Formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection of infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels on the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Representative illustrations of methods suitable for the preparation of compounds of the present invention are shown in Schemes I and II. Those having skill in the art will recognize that the starting materials may be varied and additional steps employed to produce compounds encompassed by the present invention.

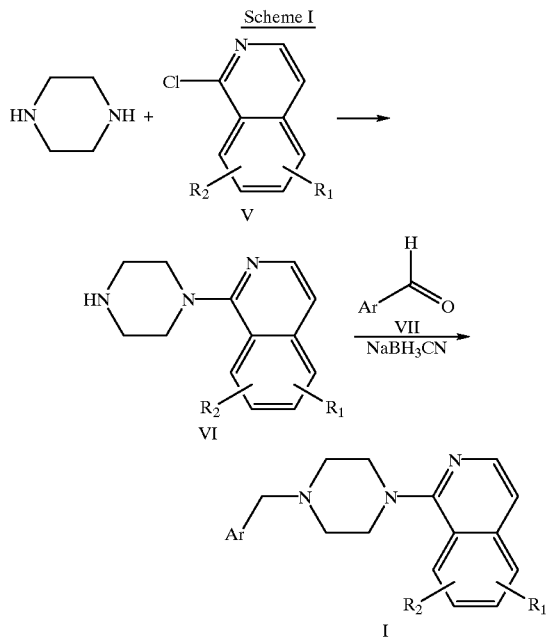

wherein Ar, $R_1$ and $R_2$ are as defined above for Formula I.

As depicted in Scheme I, a suitably substituted 1-chloroisoquinoline of Formula V is condensed with piperazine to provide a 1-isoquinolin-1-ylpiperazine of Formula VI. The compound of Formula VI is typically reductively alkylated with an arylaldehyde of Formula VII with a reducing agent such as, for example, sodium cyanoborohydride to yield the desired 1-(1-isoquinolin-1-yl)-4-(1-phenylmethyl)piperazine of Formula I. In certain situations, protection of reactive moieties such as nitrogen and hydroxy groups will be necessary to allow a conversion to be achieved without adversely affecting the reactive moiety. Those having skill in the art will recognize suitable protecting groups and methods for facilitating removal of the protecting groups. The protecting groups can be added and removed using methods taught in the literature or analogous methods.

Alternatively, compounds of Formula I may be prepared according to Scheme II

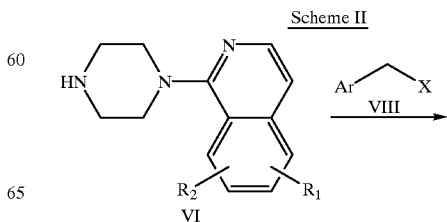

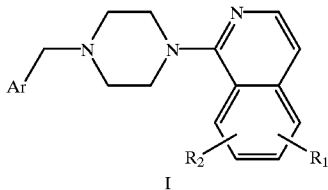

wherein Ar, $R_1$ and $R_2$ are as defined above for Formula I.

As shown in Scheme II, a 1-isoquinolin-1-ylpiperazine of Formula VI (prepared as shown above in Scheme I) may be alkylated using an arylmethylhalide compound of Formula VIII to provide the desired 1-(isoquinolin-1-yl)-4-(1-arylmethyl)piperazine of Formula 1. Again, when necessary reactive groups may be protected according to literature methods or modified literature methods.

The disclosures in this application of all articles and references, including patents, are incorporated herein by reference.

Those having skill in the art will recognize that the starting materials may be varied and additional steps employed to produce compounds encompassed by the present invention.

The invention is illustrated further by the following examples which are not to be construed as limiting the invention in scope or spirit to the specific procedures and compounds described in them.

EXAMPLE 1

1. 1-(Isoquinolin-1-yl)piperazine

A solution of 2-chloroisoquinoline (5 g) in 20 mL of toluene is added dropwise to a refluxing solution of piperazine (20 g) in 150 mL of toluene. The solution is heated for an additional 48 h. After cooling to 0° C. for 0.5 h, the solution is filtered. The filtrate is then extracted with 10% acetic acid. The aqueous extracts are washed with ether, basified and subsequently extracted with dichloromethane. The dichloromethane layer is finally washed with water, dried and concentrated. The material is placed under vacuum overnight to yield the title compound (6.8 g, m.p. 54–56° C.). $^1$H NMR (CDCl$_3$) 8.14 (d, J=5.5 Hz, 1 H), 8.10 (d, J=8.5 Hz, 1 H), 7.74 (d, J=8.5 Hz, 1 H), 7.60 (t, J=7.2 Hz, 1 H), 7.50 (t, J=7.6 Hz, 1 H), 7.24 (d, J=5.5 Hz, 1 H), 3.39 (t, J=5.0Hz, 4 H), 3.16 (t, J=5.0Hz, 4 H).

2. 1-(Isoquinolin-1-yl)-4-(1-[piperonyl]methyl)piperazine hydrochloride

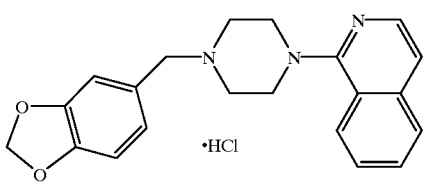

A solution of 1-(isoquinolin-1-yl)piperazine (215 mg, 1.0 mmol) and piperonal (160 mg) in methanol (10 mL) is prepared and adjusted to pH 4 using acetic acid. Sodium cyanoborohydride (500 mg) is then added and the reaction mixture allowed to stir at room temperature overnight. The solvent is evaporated and the residual oil partitioned between dichloromethane and 5% aqueous ammonia. The organic layer is then subjected to preparative TLC (10:2 hexane:ethylacetate) which yields the free base of the title compound as a colorless oil (300 mg). The hydrochloride salt is then obtained from an ethylacetate solution after treatment with hydrochloric acid (m.p.250–251° C.). $^1$H NMR (CDCl$_3$) 8.15 (d, J=5.5 Hz, 1 H), 8.06 (d, J=8.5 Hz, 1 H), 7.75 (d, J=8.0 Hz, 1 H), 7.65 (t, J=7.0 Hz, 1 H), 7.48 (t, J=7.6 Hz, 1 H), 7.23 (d, J=6.1 Hz, 1 H), 6.91 (s, 1 H), 6.80 (m, 2 H), 3.55 (s, 2 H), 3.43 (s br, 4 H), 2.71 (s br, 4 H).

EXAMPLE 2

1-(Isoquinolin-1-yl)-4-(1-[4-chlorophenyl]methyl) piperazine oxalate

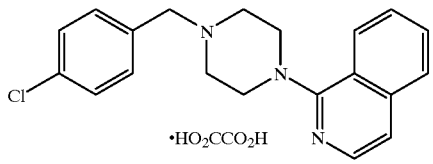

A solution of 1-(isoquinolin-1-yl)piperazine (215 mg, 1.0 mmol) and 4-chlorobenzyl chloride (180 mg) in acetonitrile (10 mL) containing potassium carbonate (500 mg) is stirred and heated at 60° C. for 4 h. After cooling, the reaction mixture is partitioned between ether and water. The organic layer was extracted with 1 N HCl. The acidic extract is then basified and extracted with chloroform. The resulting organic layer is dried and concentrated to provide the free base of the title compound as a white solid ( 300 mg, 88%).

The oxalate salt is prepared from isopropanol (m.p.207–208° C.). $^1$H NMR (DMSO) 8.09 (d, J=5.5 Hz, 1 H), 8.06 (d, J=8.5 Hz, 1 H), 7.87 (d, J=8.0 Hz, 1 H), 7.69 (t, J=7.0 Hz, 1 H), 7.58 (t, J=7.6 Hz, 1 H), 7.46 (s br, 4 H), 7.40 (d, J=6.1 Hz, 1 H), 3.93 (s br, 2 H), 3.40 (s br, 4 H), 2.95 (s br, 4 H).

EXAMPLE 3

The following compounds are prepared essentially according to the procedures set forth above in Examples 1 and 2.

1-(isoquinolin-1-yl)-4-(1-[3,4-difluorophenyl]methyl) piperazine oxalate (m.p. 212–213° C.).

1-(isoquinolin-1-yl)-4-(1-[3,5-difluorophenyl]methyl) piperazine oxalate (m.p. 223–224° C.).

1-(isoquinolin-1-yl)-4-(1-[2-naphthyl]methyl)piperazine hydrochloride (m.p. 265–268° C.).

1-(isoquinolin-1-yl)-4-(1-[4-methylphenyl]methyl) piperazine oxalate (m.p. 192–194° C.).

1-(isoquinolin-1-yl)-4-(1-[3-chlorophenyl]methyl) piperazine.

EXAMPLE 4

The pharmaceutical utility of compounds of this invention is indicated by the following assays for dopamine receptor subtype affinity.

1. Assay For $D_2$ And $D_4$ Receptor Binding Activity

Pellets of COS cells containing recombinantly produced $D_2$ or $D_4$ receptors from African Green monkey are used for the assays. The sample is homogenized in 100 volumes (w/vol) of 0.05 M Tris HCl buffer at 4° C. and pH 7.4. The sample is then centrifuged at 30,000×g and resuspended and rehomogenized. The sample is again centrifuged as described above and the final tissue sample is frozen until use. The tissue is resuspended 1:20 (wt/vol) in 0.05 M Tris HCl buffer containing 100 mM NaCl.

Incubations are carried out at 48° C. and contain 0.4 ml of tissue sample, 0.5 nM $^3$H-YM 09151-2 and the compound of interest in a total incubation of 1.0 ml. Nonspecific binding is defined as that binding found in the presence of 1 mM spiperone; without further additions, nonspecific binding is less than 20% of total binding. Binding characteristics for representative examples of this invention for the $D_2$ and $D_4$ receptor subtypes are shown in Table 2 below for rat striatal homogenates. The binding characteristics of compounds of Formula I for the $D_4$ receptor, expressed in nM, generally range from about 0.5 nanomolar (nM) to about 25 nanomolar (nM). These compounds typically have binding constants for the $D_2$ receptor of from about 200 nM to more than 1000 nM. Thus, the compounds of the invention are generally at least about 10 time more selective for the $D_4$ receptor than the $D_2$ receptor. More preferably, these compounds are at least 20, and more preferably at least 25–50, times more selective for the $D_4$ receptor than the $D_2$ receptor.

TABLE 2

Binding characteristics of 1-(isoquinolin-1-yl)-4-(1-phenylmethyl)piperazines to $D_4$ and $D_2$ receptors

| Compound Number[1] | $D_4 K_i$ (nM) | $D_2 K_i$ (nM) |
| --- | --- | --- |
| 1 | 5 | 556 |
| 2 | 13 | 1003 |
| 4 | 19 | ND |
| 6 | 9 | 220 |

[1]Compound numbers relate to compounds shown in Table 1.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound of the formula:

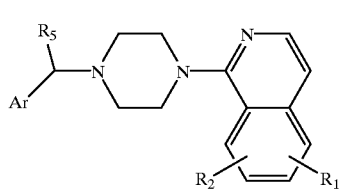

I or pharmaceutically acceptable addition salts thereof wherein:
Ar Ar is phenyl monosubstituted with $C_1$–$C_6$ alkyl or mono- or disubstituted with halogen;
$R_1$ and $R_2$ independently represent hydrogen, halogen, $C_1$–$C_6$ alkyl, $C_1$–$C_4$ alkoxy, $C_1$–$C_4$ alkylthio, hydroxy, amino, mono- or di ($C_1$–$C_6$) alkyl amino, cyano or trifluoromethyl; and
$R_5$ represents hydrogen or $C_1$–$C_6$ alkyl.

2. A compound according to claim 1, wherein Ar is phenyl substituted with methyl or mono- or disubstituted with fluoride or chloride.

3. A compound according to claim 1, wherein at least one of the substituents on the phenyl group is in a position para to the point of attachment of the phenyl group to the methylpiperazine.

4. A compound of the formula:

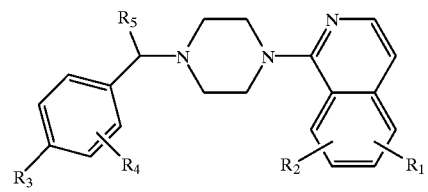

or pharmaceutically acceptable addition salts thereof wherein:
$R_1$ and $R_2$ independently represent hydrogen, halogen, $C_1$–$C_6$ alkyl, $C_1$–$C_4$ alkoxy, $C_1$–$C_4$ alkylthio, hydroxy, amino, mono- or di($C_1$–$C_6$)alkyl amino, cyano or trifluoromethyl;
$R_3$ and $R_4$ are the same or different and represent hydrogen, halogen, hydroxy, $C_1$–$C_6$ alkyl, trifluoromethyl, trifluoromethoxy or $SO_2NH_2$, provided that not both $R_3$ and $R_4$ are hydrogen; and
$R_5$ represents hydrogen or $C_1$–$C_6$ alkyl.

5. A compound according to claim 4, wherein $R_5$ is hydrogen.

6. A compound according to claim 4, wherein $R_1$ and $R_2$ are hydrogen.

7. A compound according to claim 1, wherein Ar is

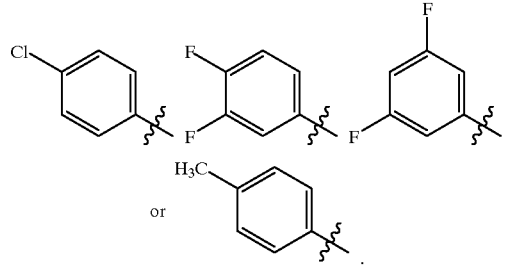

8. A compound of the formula:

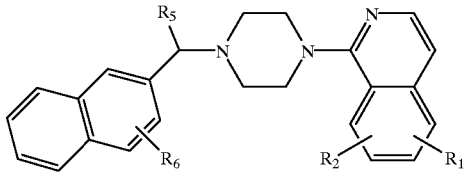

or pharmaceutically acceptable addition salts thereof wherein:
$R_1$ and $R_2$ independently represent hydrogen, halogen, $C_1$–$C_6$ alkyl, $C_1$–$C_4$ alkoxy, $C_1$–$C_4$ alkylthio, hydroxy, amino, mono- or di($C_1$–$C_6$)alkyl amino, cyano or trifluoromethyl;
$R_6$ represents hydrogen, halogen, hydroxy, $C_1$–$C_6$ alkyl, trifluoromethyl, trifluoromethoxy or $SO_2NH_2$; and
$R_5$ represents hydrogen or $C_1$–$C_6$ alkyl.

9. A compound according to claim 1 which is 1-(isoquinolin-1-yl)-4-(1-[4-chlorophenyl]methyl) piperazine.

10. A compound according to claim 1 which is 1-(isoquinolin-1-yl)-4-(1-[3,5-difluorophenyl]methyl) piperazine.

11. A compound according to claim 1 which is 1-(isoquinolin-1-yl)-4-(1-[3,4-difluorophenyl]methyl) piperazine.

12. A compound according to claim 1 which is 1-(isoquinolin-1-yl)-4-(1-[2-naphthyl]methyl)piperazine.

13. A compound according to claim 1 which is 1-(isoquinolin-1-yl)-4-(1-[3-chlorophenyl]methyl)piperazine.

14. A compound according to claim 1 which is 1-(isoquinolin-1-yl)-4-(1-[4-methylphenyl]methyl)piperazine.

* * * * *